(12) United States Patent
Daubresse et al.

(10) Patent No.: US 10,524,999 B2
(45) Date of Patent: Jan. 7, 2020

(54) COMPOSITION COMPRISING A COMBINATION OF PARTICULAR ALKOXYSILANES AND A FATTY SUBSTANCE

(71) Applicant: L'OREAL, Paris (FR)

(72) Inventors: Nicolas Daubresse, La Celle Saint-Cloud (FR); Julien Cabourg, Combs la Ville (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/061,800

(22) PCT Filed: Dec. 14, 2016

(86) PCT No.: PCT/EP2016/081025
§ 371 (c)(1),
(2) Date: Jun. 13, 2018

(87) PCT Pub. No.: WO2017/102857
PCT Pub. Date: Jun. 22, 2017

(65) Prior Publication Data
US 2018/0369108 A1    Dec. 27, 2018

(30) Foreign Application Priority Data

Dec. 14, 2015 (FR) .................................. 15 62331
Dec. 14, 2015 (FR) .................................. 15 62332

(51) Int. Cl.
| | | |
|---|---|---|
| *A61K 8/58* | (2006.01) | |
| *A61K 8/31* | (2006.01) | |
| *A61K 8/34* | (2006.01) | |
| *A61K 8/37* | (2006.01) | |
| *A61Q 5/06* | (2006.01) | |
| *A61Q 5/12* | (2006.01) | |
| *A61K 8/92* | (2006.01) | |

(52) U.S. Cl.
CPC ............... *A61K 8/585* (2013.01); *A61K 8/31* (2013.01); *A61K 8/342* (2013.01); *A61K 8/37* (2013.01); *A61K 8/922* (2013.01); *A61Q 5/06* (2013.01); *A61Q 5/12* (2013.01); *A61K 2800/5922* (2013.01); *A61K 2800/95* (2013.01)

(58) Field of Classification Search
None
See application file for complete search history.

(56) References Cited

U.S. PATENT DOCUMENTS

| | | |
|---|---|---|
| 2,047,398 A | 7/1936 | Voss et al. |
| 2,102,113 A | 12/1937 | Djordjevitch |
| 2,463,264 A | 3/1949 | Graenacher et al. |
| 2,723,248 A | 11/1955 | Wright |
| 2,798,053 A | 7/1957 | Brown |
| 2,923,692 A | 2/1960 | Ackerman et al. |
| 3,579,629 A | 5/1971 | Pasero et al. |
| 3,810,977 A | 5/1974 | Levine et al. |
| 3,915,921 A | 10/1975 | Schlatzer, Jr. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,128,631 A | 12/1978 | Lundmark et al. |
| 4,131,576 A | 12/1978 | Iovine et al. |
| 4,137,208 A | 1/1979 | Elliott |
| 4,237,243 A | 12/1980 | Quack et al. |
| 4,282,203 A | 8/1981 | Jacquet et al. |
| 4,289,752 A | 9/1981 | Mahieu et al. |
| 4,509,949 A | 4/1985 | Huang et al. |
| 4,585,597 A | 4/1986 | Lang et al. |
| 5,064,641 A | 11/1991 | Lang et al. |
| 5,089,578 A | 2/1992 | Valint et al. |
| 5,585,091 A | 12/1996 | Pelzer et al. |
| 5,618,523 A | 4/1997 | Zysman et al. |
| 5,773,611 A | 6/1998 | Zysman et al. |
| 6,822,039 B1 | 11/2004 | Monfreux-Gaillard et al. |
| 6,953,584 B1 | 10/2005 | Samain et al. |
| 2008/0226576 A1 | 9/2008 | Benabdillah et al. |
| 2011/0200654 A1 | 8/2011 | Habar |
| 2013/0255709 A1 | 10/2013 | Khenniche et al. |

FOREIGN PATENT DOCUMENTS

| | | |
|---|---|---|
| DE | 2330956 A1 | 1/1974 |
| EP | 0159628 A2 | 10/1985 |
| EP | 0173109 A2 | 3/1986 |

(Continued)

OTHER PUBLICATIONS

Anonymous: "Collacral Val Technical Information," XP055340344, Apr. 1, 2015, p. 1. Retrieved from the Internet: https://www.dispersions-pigments.basf.com/portal/load/fid819942/TI_ED_1927_e_Collacral_VAL_187214_SCREEN_01.pdf [retrieved on Jan. 30, 2017].

International Search Report for counterpart Application PCT/EP2016/081024, dated Feb. 8, 2017.

Fonnum, G., et al., "Associative Thickeners. Part I: Synthesis, Rheology and Aggregation Behavior," Colloid Polym. Sci., 271, (1993) pp. 380-389.

Morishima, Yotaro, "Self-Assembling Amphiphilic Polyelectrolytes and their Nanostructures," Chinese Journal of Polymer Science, vol. 18, No. 40, (2000), pp. 323-336.

(Continued)

*Primary Examiner* — Brian J Davis
(74) *Attorney, Agent, or Firm* — The Marbury Law Group, PLLC (57) ABSTRACT

The invention relates to a composition comprising: (a) one or more alkoxysilanes bearing solubilizing function(s) of formula $R_1Si(OR_2)_z(R_3)_x(OH)_y$, and/or hydrolysis products thereof and/or oligomers thereof, (b) one or more alkylalkoxysilanes of formula $(R_4)_mSi(OR_5)_n$ and/or hydrolysis products thereof and/or oligomers thereof, and (c) one or more fatty substances. The invention also relates to the use of said composition for shaping and/or conditioning the hair.

16 Claims, 1 Drawing Sheet

(56) References Cited

FOREIGN PATENT DOCUMENTS

| | | | |
|---|---|---|---|
| EP | 0503853 | A2 | 9/1992 |
| EP | 0669323 | A1 | 8/1995 |
| EP | 0750899 | A2 | 1/1997 |
| EP | 1736139 | A1 | 12/2006 |
| FR | 1222944 | A | 6/1960 |
| FR | 1564110 | A | 4/1969 |
| FR | 1580545 | A | 9/1969 |
| FR | 2198719 | A1 | 4/1974 |
| FR | 2265781 | A1 | 10/1975 |
| FR | 2265782 | A1 | 10/1975 |
| FR | 2350384 | A1 | 12/1977 |
| FR | 2357241 | A2 | 2/1978 |
| FR | 2416723 | A1 | 9/1979 |
| FR | 2439798 | A1 | 5/1980 |
| FR | 2528420 | A1 | 12/1983 |
| FR | 2639347 | A1 | 5/1990 |
| FR | 2673179 | A1 | 8/1992 |
| FR | 2783164 | A1 | 3/2000 |
| FR | 2910275 | A1 | 6/2008 |
| FR | 2910276 | A1 | 6/2008 |
| FR | 2937248 | A1 | 4/2010 |
| FR | 2964869 | A1 | 3/2012 |
| FR | 2966355 | A1 | 4/2012 |
| FR | 2966356 | A1 | 4/2012 |
| FR | 3004932 | A1 | 10/2014 |
| FR | 3004933 | A1 | 10/2014 |
| FR | 3008888 | A1 | 1/2015 |
| GB | 839805 | A | 6/1960 |
| GB | 922457 | A | 4/1963 |
| GB | 1408388 | A | 10/1975 |
| GB | 1572626 | A | 7/1980 |
| LU | 75370 | A1 | 2/1978 |
| LU | 75371 | A1 | 2/1978 |
| WO | 98/44012 | A1 | 10/1998 |
| WO | 00/31154 | A1 | 6/2000 |
| WO | 00/68282 | A1 | 11/2000 |
| WO | 01/22931 | A1 | 4/2001 |
| WO | 2007/032314 | A1 | 3/2007 |
| WO | 2012038880 | A2 | 3/2012 |
| WO | 2012055805 | A1 | 5/2012 |
| WO | 2013/083760 | A2 | 6/2013 |
| WO | 2014/177628 | A1 | 11/2014 |
| WO | 2015011258 | A1 | 1/2015 |
| WO | 2017/102856 | A1 | 6/2017 |

OTHER PUBLICATIONS

Noda, Tetsuya, et al., "Micelle Formation of Random Copolymers of Sodium 2-(Acrylamido)-2-Methylpropanesulphonate and a Nonionic Surfactant Macromonomer in Water as Studied by Fluorescence and Dynamic Light Scattering," Macromolecules 2000, 33, pp. 3694-3704.

Noda, Tetsuya et al., "Solution Properties of Micelle Networks Formed by Nonionic Surfactant Moieties Covalently Bound to a Polyelectrolyte: Salt Effects on Rheological Behavior," Langmuir 2000, 16, pp. 5324-5332.

Noda, Tetsuya, et al., "Stimuli-Responsive Amphiphilic Copolymers of Sodium 2-(Acrylamido)-2-Methylpropanesulphonate and Associative Macromonomers," Polym. Preprint, Div. Polym. Chem. 1999, 40(2), pp. 220-221.

Todd, Charles, et al., "Volatile Silicone Fluids for Cosmetic Formulations," Cosmetics and Toiletries, vol. 91, Jan. 1976, pp. 29-32.

Wertz, et al., Essential Fatty Acids and Epidermal Integrity, Archive of Dermatology, vol. 123, Oct. 1987, pp. 1381-1384.

International Search Report for Application No. PCT/EP2016/081025, dated Feb. 8, 2017.

COMPOSITION COMPRISING A COMBINATION OF PARTICULAR ALKOXYSILANES AND A FATTY SUBSTANCE

CROSS REFERENCE TO RELATED APPLICATIONS

This is a national stage application of PCT/EP2016/081025, filed internationally on Dec. 14, 2016, which claims priority to French Application Nos. 1562332 filed on Dec. 14, 2015, and 1562331 filed on Dec. 14, 2015, all of which are incorporated by reference herein in their entireties.

The present invention relates to a composition comprising a combination of particular alkoxysilanes and at least one fatty substance, to the use thereof for the cosmetic treatment of keratin fibres and to a cosmetic treatment process using this composition.

In the field of the cosmetic treatment of keratin fibres, especially human keratin fibres such as the hair, and more particularly in the field of hairstyling and haircare, rinse-out products but also leave-in products are used. These products are directed towards giving the head of hair shaping properties, such as improved curl definition for curly hair, manageability for straight hair, and limitation of the appearance of frizziness or tufts.

In addition, it is expected that these products will provide long-lasting properties, in particular over a day, especially as regards the resistance to moisture and to mechanical stresses due to the movement of the head of hair, or else over a longer period, for example after one or even more shampoo washes.

Thus, it is sought to obtain hair properties that are modified so as to simplify routine styling operations, for example by affording shaping and care that are efficient while at the same time being discreet, and without feeling greasy, tacky or, on the contrary, coarse or wooden.

Several types of products and technologies are currently available both to hairstylists and to consumers. The first hairsetting lotions, based on water, alcohol and polymers, were followed by the arrival of styling mousses, still based on polymers, and two-phase systems, but also oils and sera based either on plant oils or mineral oils and most particularly based on silicones.

Plant oils make it possible to enhance the beauty of the head of hair by giving it tonicity and sheen, when they are used in small amounts and applied preferably in the evening, and then partially removed by shampooing.

Mineral oils are reserved for caring for very damaged hair, such as hair that has been relaxed by strongly alkaline treatments. Silicone oils, such as linear or cyclic volatile silicones, and polydimethylsiloxanes of higher molecular weights, occasionally functionalized with hydroxyl or amine functions, are themselves widely used for treating the ends of the hair, for giving them a smoother feel and making them less dull and more manageable.

However, the majority of the technologies must be used parsimoniously, to limit the risk of both feeling greasy and looking dirty.

More recently, silane-based products have been developed, which can reinforce the hair fibre and afford relatively long-lasting care. Mention may be made of care solutions and creams based on aminopropyltriethoxysilane, mixed systems based on aminopropyltriethoxysilane and fatty-chain alkoxysilanes, but also two-phase systems based on aminopropyltriethoxysilane (in aqueous phase) and resin obtained by condensation of propylsilanetriol (in organic phase). These products can afford relatively long-lasting but sparingly intense performance. Furthermore, it remains very difficult to obtain a good balance between stability, ease of application and performance.

There is thus a need to develop hairstyling and haircare compositions that can overcome the drawbacks mentioned above.

The Applicant has now discovered that the combined use of at least two different particular alkoxysilanes in a composition containing at least one fatty substance makes it possible to obtain products that afford care such as a smooth feel, sheen, tonicity and ease of disentangling, which is immediate and long-lasting, without a greasy or tacky feel. In particular, long-lasting shaping effects are obtained, most particularly for curl definition in the case of curly hair, or manageability for straight hair, these effects being especially resistant to moisture, and without having to overload with fatty substance or tack.

In addition, the compositions according to the invention can give the hair care properties that are found even after shampooing several times, with, especially, a sensation of more supple wet hair and greater ease of disentangling.

Furthermore, said compositions improve the durability of colouring effects with respect to shampooing.

The subject of the invention is thus a composition comprising:
(a) one or more alkoxysilanes bearing solubilizing function(s) of formula (I) below, and/or hydrolysis products thereof and/or oligomers thereof:

$$R_1Si(OR_2)_z(R_3)_x(OH)_y \quad (I)$$

in which:
$R_1$ is a linear or branched, saturated or unsaturated, cyclic or acyclic $C_1$-$C_6$ hydrocarbon-based chain substituted with one or more groups chosen from the following groups:
  amine $NH_2$ or NHR, R being:
    a $C_1$-$C_{20}$ and preferably $C_1$-$C_6$ alkyl group optionally substituted with a group comprising a silicon atom,
    a $C_3$-$C_{40}$ cycloalkyl group or
    a $C_6$-$C_{30}$ aromatic group,
  hydroxyl,
  thiol,
  aryl or aryloxy substituted with an amino group or with a $C_1$-$C_4$ aminoalkyl group,
$R_1$ possibly being interrupted with a heteroatom such as O, S or NH, or a carbonyl group (CO),
$R_2$ and $R_3$, which may be identical or different, represent a linear or branched alkyl group comprising from 1 to 6 carbon atoms,
y denotes an integer ranging from 0 to 3,
z denotes an integer ranging from 0 to 3, and
x denotes an integer ranging from 0 to 2,
with z+x+y=3,
(b) one or more alkylalkoxysilanes of formula (III) below, and/or hydrolysis products thereof and/or oligomers thereof:

$$(R_4)_m Si(OR_5)_n \quad (III)$$

in which:
$R_4$ and $R_5$ each represent, independently of each other, a $C_{1-6}$, better still $C_{1-4}$, alkyl group such as methyl, ethyl, n-propyl, isopropyl, n-butyl, isobutyl and tert-butyl, preferably methyl, ethyl or n-propyl, n ranges from 1 to 3,
m ranges from 1 to 3,
on condition that m+n=4,
and
(c) one or more fatty substances.

A subject of the present invention is also the use of a composition according to the invention for shaping and/or conditioning the hair.

Another subject of the invention consists of a cosmetic treatment process, and more particularly a process for shaping and/or conditioning the hair, comprising the use of the composition according to the invention.

Other subjects, characteristics, aspects and advantages of the invention will emerge even more clearly on reading the description and the examples that follow, and the attached figures.

In the text hereinbelow, unless otherwise indicated, the limits of a range of values are included in that range, in particular in the expressions "between" and "ranging from . . . to . . . ".

The expression "at least one" used in the present description is equivalent to the expression "one or more".

According to the invention, the composition comprises:
(a) one or more alkoxysilanes bearing solubilizing function(s) of formula (I) as defined in the present application, and/or hydrolysis products thereof and/or oligomers thereof,
(b) one or more alkylalkoxysilanes of formula (III) as defined in the present application, and/or hydrolysis products thereof and/or oligomers thereof, and
(c) one or more fatty substances.

The term "oligomer" used in the invention means the polymerization products of the compounds to which the term "oligomer" relates, comprising from 2 to 10 silicon atoms In the present invention, the expression "alkoxysilane(s) bearing solubilizing function(s) (a)" covers the alkoxysilane(s) bearing solubilizing function(s) of formula (I) below, and/or hydrolysis product(s) thereof and/or oligomer(s) thereof:

$$R_1Si(OR_2)_z(R_3)_x(OH)_y \quad (I)$$

in which:
$R_1$ is a linear or branched, saturated or unsaturated, cyclic or acyclic $C_1$-$C_6$ hydrocarbon-based chain substituted with one or more groups chosen from the following groups:
  amine $NH_2$ or NHR, R being:
    a $C_1$-$C_{20}$ and preferably $C_1$-$C_6$ alkyl group optionally substituted with a group comprising a silicon atom,
    a $C_3$-$C_{40}$ cycloalkyl group or
    a $C_6$-$C_{30}$ aromatic group,
  hydroxyl,
  thiol,
  aryl or aryloxy substituted with an amino group or with a $C_1$-$C_4$ aminoalkyl group,
$R_1$ possibly being interrupted with a heteroatom (O, S or NH) or a carbonyl group (CO),
$R_2$ and $R_3$, which may be identical or different, represent a linear or branched alkyl group comprising from 1 to 6 carbon atoms,
y denotes an integer ranging from 0 to 3,
z denotes an integer ranging from 0 to 3, and
x denotes an integer ranging from 0 to 2,
with z+x+y=3.

More particularly, the alkoxysilanes bearing solubilizing function(s) (a) comprise at least one amino group in their structure.

Preferably, $R_1$ is an acyclic chain.

Preferably, $R'_1$ is a linear or branched, saturated or unsaturated $C_1$-$C_6$ hydrocarbon-based chain, substituted with an amine group $NH_2$ or NHR, R being:
  a $C_1$-$C_{20}$ and preferably $C_1$-$C_6$ alkyl group optionally substituted with a group comprising a silicon atom, better still a group $(R_2O)_3Si-$,
  a $C_3$-$C_{40}$ cycloalkyl group or
  a $C_6$-$C_{30}$ aromatic group.

Preferably, $R_2$ represents an alkyl group comprising from 1 to 4 carbon atoms, better still a linear alkyl group comprising from 1 to 4 carbon atoms, and is preferably the ethyl group.

Preferably, $R_3$ represents an alkyl group comprising from 1 to 4 carbon atoms, better still a linear alkyl group comprising from 1 to 4 carbon atoms, and preferably represents a methyl group or an ethyl group.

Preferably, the compound of formula (I) comprises only one or two silicon atoms in its structure.

Preferably, z ranges from 1 to 3. Even more preferentially, z is equal to 3 and thus x=y=0.

Preferably, the alkoxysilane(s) bearing solubilizing function(s) (a) according to the invention are chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxy-silane, p-aminophenyltrimethoxysilane, N-(2-aminoethylaminomethyl)phenethyl-trimethoxysilane and bis[3-(triethoxysilyl)propyl]amine, oligomers thereof, hydrolysis products thereof and a mixture of these compounds, better still from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane and bis[3-(triethoxysilyl)propyl]amine, oligomers thereof, hydrolysis products thereof and a mixture of these compounds, and in particular the alkoxysilane(s) bearing solubilizing function(s) (a) are chosen from 3-aminopropyltriethoxysilane (APTES), hydrolysis products thereof, oligomers thereof and a mixture of these compounds.

According to one preferred embodiment, the alkoxysilane(s) bearing solubilizing function(s) (a) are chosen from the compounds of formula (II) below, and/or oligomers thereof and/or hydrolysis products thereof:

$$H_2N(CH_2)_{n''}-Si(OR')_3 \quad (II)$$

in which the groups R', which may be identical or different, are chosen from linear or branched $C_1$-$C_6$ alkyl groups and n" is an integer ranging from 1 to 6 and preferably from 2 to 4.

An alkoxysilane bearing solubilizing function(s) (a) that is particularly preferred according to this embodiment is 3-aminopropyltriethoxysilane (APTES) and/or hydrolysis products thereof and/or oligomers thereof.

Said alkoxysilane(s) bearing solubilizing function(s) (a) used in the composition according to the invention may represent from 0.5% to 50% by weight, preferably from 1% to 30% by weight, and in particular from 2% to 25% by weight, relative to the total weight of the composition.

The second essential ingredient (b) of the composition of the invention is an alkylalkoxysilane of formula (III) below, and/or hydrolysis products thereof and/or oligomers thereof:

$$(R_4)_m Si(OR_5)_n \qquad (III)$$

in which:
$R_4$ and $R_5$ each represent, independently of each other, a $C_{1-6}$, better still $C_{1-4}$, alkyl group such as methyl, ethyl, n-propyl, isopropyl, n-butyl, isobutyl and tert-butyl, preferably methyl, ethyl or n-propyl,
n ranges from 1 to 3,
m ranges from 1 to 3,
on condition that m+n=4.

Preferably, $R_5$ represents a methyl, ethyl or n-propyl group, n=3 and m=1.

Preferably, the oligomers of the compounds of formula (III) are water-soluble.

As examples of alkylalkoxysilanes (b) that are particularly preferred, mention may be made especially of methyltriethoxysilane (MTES), methyltripropoxysilane, oligomers thereof and/or hydrolysis products thereof.

In the present invention, the term "alkylalkoxysilane(s) (b)" encompasses the alkylalkoxysilane(s) of formula (III), and/or hydrolysis product(s) thereof and/or oligomer(s) thereof.

Said alkylalkoxysilanes (b) used in the composition according to the invention may represent from 0.1% to 50% by weight, preferably from 0.2% to 20% by weight, preferentially from 0.5% to 15% by weight, and in particular from 1% to 10% by weight, relative to the total weight of the composition.

These two compounds (a) and (b) are preferably present in the composition according to the invention in an (a)/(b) weight ratio ranging from 0.5 to 10, more preferentially from 1 to 10, better still from 1.5 to 7.

The composition according to the invention comprises, as third essential ingredient, one or more fatty substances.

The term "fatty substance" means an organic compound that is insoluble in water at standard temperature (25° C.) and at atmospheric pressure (760 mmHg, i.e. $1.013 \times 10^5$ Pa), i.e. with a solubility of less than 5%, preferably of less than 1% and even more preferably of less than 0.1%.

The fatty substances are generally soluble in organic solvents under the same temperature and pressure conditions, for instance chloroform, ethanol, benzene, liquid petroleum jelly or decamethylcyclopentasiloxane.

The fatty substances may be solid or liquid, preferably liquid.

The liquid fatty substances that may be used in the invention are liquid at room temperature (25° C.) and at atmospheric pressure (760 mmHg; i.e. $1.013 \times 10^5$ Pa). They preferably have a viscosity of less than or equal to 2 Pa·s, better still less than or equal to 1 Pa·s, and even better still less than or equal to 0.1 Pa·s at a temperature of 25° C. and at a shear rate of 1 s$^{-1}$.

The liquid fatty substances that may be used in the composition according to the invention are generally not oxyalkylenated and preferably do not contain any carboxylic acid COOH functions.

Preferably, the liquid fatty substances are chosen from hydrocarbons, fatty alcohols, fatty esters, fatty ethers and silicones, and mixtures thereof.

Even more preferentially, they are chosen from hydrocarbons, fatty alcohols, fatty esters and silicones, which are preferably volatile, and mixtures thereof.

The term "liquid hydrocarbon" means a hydrocarbon composed solely of carbon and hydrogen atoms, which is liquid at standard temperature (25° C.) and at atmospheric pressure (760 mmHg, i.e. $1.013 \times 10^5$ Pa), of mineral, plant or synthetic origin.

More particularly, the liquid hydrocarbons are chosen from:
linear or branched, optionally cyclic, $C_6$-$C_{16}$ alkanes. Examples that may be mentioned include hexane, undecane, dodecane, tridecane, and isoparaffins, for instance isohexadecane, isododecane and isodecane, and mixtures thereof.
linear or branched hydrocarbons of mineral, animal or synthetic origin with more than 16 carbon atoms, such as liquid paraffins, liquid petroleum jelly, polydecenes, hydrogenated polyisobutene such as the product sold under the brand name Parleam® by NOF Corporation, and squalane.

In a preferred variant, the liquid hydrocarbon(s) are chosen from linear or branched, optionally cyclic, $C_6$-$C_{16}$ alkanes.

The term "liquid fatty alcohol" means a non-glycerolated and non-oxyalkylenated fatty alcohol which is liquid at ordinary temperature (25° C.) and at atmospheric pressure (760 mmHg, i.e. $1.013 \times 10^5$ Pa).

Preferably, the liquid fatty alcohols of the invention comprise from 8 to 30 carbon atoms and better still from 8 to 20 carbon atoms.

The liquid fatty alcohols of the invention may be saturated or unsaturated.

The saturated liquid fatty alcohols are preferably branched. They may optionally comprise in their structure at least one aromatic or non-aromatic ring. Preferably, they are acyclic.

More particularly, the saturated liquid fatty alcohols of the invention are chosen from octyldodecanol, isostearyl alcohol and 2-hexyldecanol.

Octyldodecanol is most particularly preferred.

The unsaturated liquid fatty alcohols contain in their structure at least one double or triple bond, and preferably one or more double bonds. When several double bonds are present, there are preferably 2 or 3 of them, and they may be conjugated or unconjugated.

These unsaturated fatty alcohols may be linear or branched.

They may optionally comprise in their structure at least one aromatic or non-aromatic ring. Preferably, they are acyclic.

More particularly, the unsaturated liquid fatty alcohols of the invention are chosen from oleyl alcohol, linoleyl alcohol, linolenyl alcohol and undecylenyl alcohol.

Oleyl alcohol is most particularly preferred.

The term "liquid fatty ester" means an ester derived from a fatty acid and/or from a fatty alcohol, which is liquid at normal temperature (25° C.) and at atmospheric pressure (760 mmHg; i.e. $1.013 \times 10^5$ Pa).

The esters are preferably liquid esters of saturated or unsaturated and linear or branched $C_1$-$C_{26}$ aliphatic mono- or polyacids and of saturated or unsaturated and linear or branched $C_1$-$C_{26}$ aliphatic mono- or polyalcohols, the total number of carbon atoms in the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used.

Mention may be made especially of diethyl sebacate, diisopropyl sebacate, bis(2-ethylhexyl) sebacate, diisopropyl adipate, di-n-propyl adipate, dioctyl adipate, bis(2-ethylhexyl) adipate, diisostearyl adipate, bis(2-ethylhexyl) maleate, triisopropyl citrate, triisocetyl citrate, triisostearyl citrate, glyceryl trilactate, glyceryl trioctanoate, trioctyldodecyl citrate, trioleyl citrate, neopentyl glycol diheptanoate, and diethylene glycol diisononanoate.

The composition may also comprise, as liquid fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include saccharose, glucose, galactose, ribose, fucose, maltose, fructose, mannose, arabinose, xylose and lactose, and derivatives thereof, especially alkyl derivatives, such as methyl derivatives, for instance methylglucose.

The sugar and fatty acid esters may be chosen in particular from the group comprising the esters or mixtures of sugar esters described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be chosen from mono-, di-, tri- and tetraesters, and polyesters, and mixtures thereof.

These esters may be, for example, oleates, laurates, palmitates, myristates, behenates, cocoates, stearates, linoleates, linolenates, caprates and arachidonates, and mixtures thereof, such as, in particular, oleopalmitate, oleostearate or palmitostearate mixed esters.

More particularly, use is made of monoesters and diesters and especially of sucrose, glucose or methylglucose mono- or dioleates, stearates, behenates, oleopalmitates, linoleates, linolenates or oleostearates.

An example that may be mentioned is the product sold under the name Glucate® DO by Amerchol, which is a methylglucose dioleate.

Finally, use may also be made of natural or synthetic glycerol esters of mono-, di- or triacids.

Among these, mention may be made of plant oils.

As oils of plant origin or synthetic triglycerides that may be used in the composition of the invention as liquid fatty esters, examples that may be mentioned include:
triglyceride oils of plant or synthetic origin, such as liquid fatty acid triglycerides containing from 6 to 30 carbon atoms, for instance heptanoic or octanoic acid triglycerides, or alternatively, for example, sunflower oil, maize oil, soya bean oil, marrow oil, grapeseed oil, sesame oil, hazelnut oil, apricot oil, macadamia oil, arara oil, castor oil, avocado oil, olive oil, rapeseed oil, coconut oil, wheatgerm oil, sweet almond oil, safflower oil, candlenut oil, camelina oil, tamanu oil, babassu oil and pracaxi oil, caprylic/capric acid triglycerides, for instance those sold by Stéarineries Dubois or those sold under the names Miglyol® 810, 812 and 818 by Dynamit Nobel, jojoba oil and shea butter oil.

Use will preferably be made, as esters according to the invention, of liquid fatty esters resulting from monoalcohols.

Isopropyl myristate or isopropyl palmitate are particularly preferred.

The liquid fatty ethers are chosen from liquid dialkyl ethers such as dicaprylyl ether.

The liquid fatty substance(s) that may be used in the composition according to the invention may be chosen from silicones.

Preferably, the liquid silicone(s) are chosen from polydialkylsiloxanes, in particular polydimethylsiloxanes (PDMSs), and organomodified polysiloxanes comprising at least one functional group chosen from amino groups, aryl groups and alkoxy groups.

Organopolysiloxanes are defined in greater detail in Walter Noll's *Chemistry and Technology of Silicones* (1968), Academic Press. They may be volatile or non-volatile.

The liquid non-volatile silicones that may be used in the composition according to the invention may preferably be liquid non-volatile polydialkylsiloxanes, polyorganosiloxanes modified with organofunctional groups chosen from amine groups, aryl groups and alkoxy groups, and also mixtures thereof.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:
the Silbione® oils of the 47 and 70 047 series or the Mirasil® oils sold by Rhodia;
the oils of the Mirasil® series sold by Rhodia;
the oils of the 200 series from Dow Corning;
the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of the 48 series from Rhodia.

The organomodified silicones that may be used in accordance with the invention are silicones as defined above and comprising in their structure one or more organofunctional groups attached via a hydrocarbon-based group.

The organomodified silicones may be polydiarylsiloxanes, in particular polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^5$ to $5 \times 10^{-2}$ m$^2$/s at 25° C.

Among these polyalkylarylsiloxanes, examples that may be mentioned include the products sold under the following names:
- the Silbione® oils of the 70 641 series from Rhodia;
- oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Among the organomodified silicones, mention may also be made of polyorganosiloxanes comprising:
- substituted or unsubstituted amine groups, for instance the products sold under the names GP 4 Silicone Fluid and GP 7100 by Genesee. The substituted amine groups are in particular $C_1$-$C_4$ aminoalkyl groups;
- alkoxy groups such as the product sold under the name Silicone Copolymer F-755 by SWS Silicones, and Abil Wax® 2428, 2434 and 2440 by Goldschmidt.

The volatile silicones are more particularly chosen from those with a boiling point of between 60° C. and 260° C., and even more particularly from:

(i) cyclic silicones comprising from 3 to 7 and preferably 4 to 6 silicon atoms.

These are, for example, octamethylcyclotetrasiloxane sold in particular under the name Volatile Silicone 7207 by Union Carbide or Silbione 70045 V 2 by Rhodia, decamethylcyclopentasiloxane sold under the name Volatile Silicone 7158 by Union Carbide, and Silbione 70045 V 5 by Rhodia, and mixtures thereof.

Mention may also be made of cyclocopolymers of the dimethylsiloxane/methylalkylsiloxane type, such as Volatile Silicone FZ 3109 sold by Union Carbide, of chemical structure:

Mention may also be made of mixtures of cyclic silicones with organosilicon compounds, such as the mixture of octamethylcyclotetrasiloxane and tetrakis(trimethylsilyl) pentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones containing 2 to 9 silicon atoms and having a viscosity of less than or equal to $5 \times 10^{-6}$ m$^2$/s at 25° C. Examples include hexamethyldisiloxane, octamethyltrisiloxane and decamethyltetrasiloxane sold especially under the name SH 200 by Toray Silicone. Silicones belonging to this category are also described in the article published in Cosmetics and Toiletries, Vol. 91, January 76, pp. 27-32, Todd & Byers "Volatile Silicone Fluids for Cosmetics". Preferably, the linear volatile silicones contain from 2 to 7 silicon atoms and better still from 3 to 6 silicon atoms.

Preferably, the volatile silicones are chosen from cyclic silicones comprising from 4 to 6 silicon atoms and linear silicones containing 4 to 6 silicon atoms.

Preferably, the silicones are chosen from volatile silicones.

Preferably, the liquid fatty substance(s) are chosen from linear or branched $C_6$-$C_{16}$ alkanes, such as undecane, tridecane or isododecane, and mixtures thereof; triglyceride oils of plant origin such as copra oil or avocado oil; fatty esters such as isopropyl myristate; branched fatty alcohols; linear or cyclic volatile silicones, comprising less than 7 silicon atoms, preferably from 4 to 6 silicon atoms; and mixtures thereof.

Even more preferentially, the liquid fatty substances are chosen from linear or branched $C_6$-$C_{16}$ alkanes, in particular such as isododecane, undecane or tridecane, and mixtures thereof, and linear or cyclic volatile silicones, comprising less than 7 silicon atoms, preferably from 4 to 6 silicon atoms.

The term "non-liquid fatty substance" means a solid compound or a compound that has a viscosity of greater than 2 Pa·s at a temperature of 25° C. and at a shear rate of 1 s$^{-1}$.

In a first variant of the invention, the non-liquid fatty substances are chosen from non-silicone non-liquid fatty substances. Preferably, the non-silicone non-liquid fatty substances are chosen from fatty alcohols, fatty acid and/or fatty alcohol esters, non-silicone waxes, fatty amines and fatty ethers, which are non-liquid and preferably solid.

More particularly, the non-liquid fatty alcohols according to the invention are chosen from linear or branched, saturated or unsaturated alcohols containing from 8 to 30 carbon atoms.

Examples that may preferably be mentioned include cetyl alcohol, stearyl alcohol and a mixture thereof (cetylstearyl alcohol). Cetylstearyl alcohol is more particularly used.

The non-liquid esters of fatty acids and/or of fatty alcohols that may be used in the composition according to the invention are generally chosen from solid esters derived from $C_9$-$C_{26}$ fatty acids and from $C_9$-$C_{26}$ fatty alcohols.

Examples that may preferably be mentioned include octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

The non-silicone wax(es) are chosen especially from carnauba wax, candelilla wax, esparto wax, paraffin wax, ozokerite, plant waxes, such as olive tree wax, rice wax, hydrogenated jojoba wax and absolute flower waxes, such as the blackcurrant blossom essential wax sold by Bertin (France), and animal waxes, such as beeswaxes or modified beeswaxes (cerabellina), and ceramides.

The solid amides that may be used in the composition according to the invention are chosen from ceramides and ceramide analogues, such as the natural or synthetic glycoceramides corresponding to formula (IV) below:

in which:
- R' denotes a linear or branched, saturated or unsaturated alkyl radical derived from $C_{14}$-$C_{30}$ fatty acids, this radical possibly being substituted with a hydroxyl group in the alpha position, or a hydroxyl group in the omega position which is esterified with a saturated or unsaturated $C_{16}$-$C_{30}$ fatty acid;
- R" denotes a hydrogen atom or a radical (glycosyl)n, (galactosyl)m or sulfogalactosyl, in which n is an integer ranging from 1 to 4 and m is an integer ranging from 1 to 8;
- R'" denotes a $C_{15}$-$C_{26}$ hydrocarbon-based radical, saturated or unsaturated in the alpha position, this radical possibly being substituted with one or more $C_1$-$C_{14}$ alkyl radicals; with the proviso that, in the case of natural ceramides or glycoceramides, R'" may also denote a $C_{15}$-$C_{26}$ alpha-hydroxyalkyl radical, the hydroxyl group being optionally esterified with a $C_{16}$-$C_{30}$ alpha-hydroxy acid.

The ceramides that are preferred in the context of the present invention are those described by Downing in Arch. Dermatol, Vol. 123, 1381-1384, 1987, or those described in French patent FR 2 673 179.

The ceramide(s) more particularly preferred that may be used in the composition according to the invention are the compounds for which R' denotes a saturated or unsaturated alkyl derived from $C_{16}$-$C_{22}$ fatty acids; R" denotes a hydrogen atom; and R'" denotes a linear, saturated $C_{15}$ radical.

Preferentially, the following compounds may especially be chosen: N-linoleoyldihydrosphingosine, N-oleoyldihydrosphingosine, N-palmitoyldihydrosphingosine, N-stearoyldihydrosphingosine, N-behenoyldihydrosphingosine, and a mixture of these compounds.

Even more preferentially, ceramides are used for which R' denotes a saturated or unsaturated alkyl radical derived from fatty acids, R" denotes a galactosyl or sulfogalactosyl radical and R'" denotes a —CH=CH—$(CH_2)_{12}$—$CH_3$ group.

Other waxes or waxy starting materials that may be used according to the invention are especially marine waxes such as those sold by Sophim under the reference M82, and waxes of polyethylene or of polyolefins in general.

The non-liquid fatty ethers that may be used in the composition according to the invention are chosen from dialkyl ethers and especially dicetyl ether and distearyl ether, alone or as a mixture.

In a second variant of the invention, the non-liquid fatty substance(s) may be chosen from silicone non-liquid fatty substances, such as silicone gums or resins.

The silicone gums that may be used in accordance with the invention are especially polydialkylsiloxanes and preferably polydimethylsiloxanes with high number-average molecular weights ranging from 200 000 to 1 000 000, used alone or as a mixture in a solvent.

Said solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:
- mixtures formed from a hydroxy-terminated polydimethylsiloxane chain or dimethiconol (CTFA), and from a cyclic polydimethylsiloxane, also known as cyclomethicone (CTFA), such as the product Q2 1401 sold by Dow Corning;
- mixtures of a polydimethylsiloxane gum and of a cyclic silicone, such as the product SF 1214 Silicone Fluid from General Electric; this product is an SF 30 gum corresponding to a dimethicone, having a number-average molecular weight of 500 000, dissolved in the oil SF 1202 Silicone Fluid corresponding to decamethylcyclopentasiloxane;
- mixtures of two PDMSs with different viscosities, and more particularly of a PDMS gum and of a PDMS oil, such as the product SF 1236 from General Electric. The product SF 1236 is the mixture of a gum SE 30 defined above, with a viscosity of 20 $m^2$/s and of an oil SF 96 with a viscosity of $5\times10^{-6}$ $m^2$/s. This product preferably comprises 15% of gum SE 30 and 85% of an oil SF 96.

The organopolysiloxane resins that may be used in accordance with the invention are crosslinked siloxane systems containing the following units:

$(R_7)_2SiO_{2/2}$, $(R_7)_3SiO_{1/2}$, $R_7SiO_{3/2}$ and $SiO_{4/2}$ in which $R_7$ represents an alkyl containing 1 to 16 carbon atoms. Among these products, the ones that are particularly preferred are those in which $R_7$ denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by General Electric, which are silicones of dimethyl/trimethylsiloxane structure.

Mention may also be made of the trimethyl siloxysilicate-type resins sold in particular under the names X22-4914, X21-5034 and X21-5037 by Shin-Etsu.

The fatty substance(s), which are preferably liquid, are present in an amount preferably greater than or equal to 3% by weight, preferentially ranging from 3% to 99%, better still from 10% to 95% by weight, even better still from 15% to 80% by weight and even better still from 20% to 60%, relative to the total weight of the composition.

The composition may comprise a cosmetically acceptable medium. The cosmetically acceptable medium that may be used in the compositions of the invention may comprise water, one or more organic solvents, or a mixture thereof.

In one variant of the invention, the composition is anhydrous. More particularly, for the purposes of the invention, the term "anhydrous composition" means a composition with a water content of less than 5% by weight, preferably less than 2% by weight and even more preferably less than 1% by weight relative to the weight of said composition.

In another variant, the composition according to the invention is aqueous.

According to this variant, the amount of water may range from 5% to 98% by weight, better still from 15% by weight to 95% by weight, even better still from 25% to 90% by weight and even more preferentially from 30% to 85% by weight, relative to the total weight of the composition.

Preferably, the composition according to the invention is aqueous.

Examples of organic solvents that may especially be used include those that are liquid at 25° C. and $1.013\times10^5$ Pa and that are especially water-soluble, such as $C_1$-$C_7$ alcohols, especially $C_1$-$C_7$ aliphatic or aromatic monoalcohols, and $C_3$-$C_7$ polyols and polyol ethers, which may thus be used alone or as a mixture with water. Advantageously, the organic solvent may be chosen from ethanol and isopropanol, and mixtures thereof.

When it is aqueous, the pH of the composition is preferably between 3 and 11 and especially between 4 and 10.

The pH of these compositions may be adjusted to the desired value by means of basifying agents or acidifying agents that are customarily used. Among the basifying agents, examples that may be mentioned include aqueous ammonia, alkanolamines, and mineral or organic hydroxides. Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

In one preferred variant of the invention, the composition comprises at least one carboxylic acid, preferentially a hydroxy acid and even more preferentially lactic acid, so as to provide the pH stability and a satisfactory level of hydrolysis before mixing.

The composition according to the invention may also contain additives usually used in cosmetics, such as thickeners, preserving agents, fragrances and dyes, and also most of the usual cosmetic agents for hair treatments.

These additives may be present in the composition according to the invention in an amount ranging from 0 to 20% by weight, relative to the total weight of the composition.

A person skilled in the art will take care to select these optional additives and amounts thereof so that they do not harm the properties of the compositions of the present invention.

The compositions according to the invention may be prepared according to the following process: a least two aqueous phases, each comprising at least one alkoxysilane (a) or at least one alkyalkoxysilane (b), are prepared separately. The pH of each of the phases is then adjusted, when they are aqueous, before combining them.

In other variants of the invention, the composition according to the invention may be composed of several superimposed or emulsified liquid phases, or may contain suspended solid phases.

Texturing agents such as thickeners, and/or additives that are usual in cosmetics, preserving agents, fragrances and dyes, and also most of the usual cosmetic agents for hair treatments, such as cationic polymers, may be added either to at least one of the aqueous phases before mixing thereof, or after mixing thereof. In the case where it (they) are added to one of the aqueous phases before mixing, this addition will preferably be to the phase that will represent the largest part of the final composition.

A fatty phase containing at least one fatty substance is then added to the mixture of the two aqueous phases, for example in an amount at least equal to half of the total amount of the aqueous phases. Anionic, cationic, nonionic or amphoteric surfactants may also be added, to form a direct or inverse emulsion.

In another variant, one of the two alkoxysilanes (a) and (b) or both of them may be introduced directly into an oily phase, or into the phase containing at least one fatty substance, optionally followed by adding a proportion of water representing not more than two thirds of the fatty phase.

The compositions according to the invention may be in the form of a lotion, gel, cream, paste, serum, foam or emulsion.

The composition may be used on wet or dry hair, in rinse-out or leave-in mode.

A subject of the invention is also the use of the composition as defined previously for shaping and/or conditioning keratin fibres, especially human keratin fibres, and better still the hair.

The present invention also relates to a cosmetic treatment process, more particularly for shaping and/or conditioning the hair, which consists in applying to the hair an effective amount of a composition as described above and optionally in rinsing. The composition is preferably a leave-in composition.

A step of drying the keratin fibres may be envisaged in the process according to the invention, especially using a hair dryer or a straightening iron, the latter possibly heating to a temperature ranging from 150° C. to 230° C., preferably from 200 to 220° C.

The process according to the invention may also comprise:
a step of applying a composition (B) comprising one or more beneficial agents bearing anionic group(s), this application preceding or following the application of the composition according to the invention (composition (A)), and
an intermediate rinsing step which may optionally take place between the application of the two compositions (A) and (B).

This process makes it possible especially to obtain beauty-enhancing properties on the hair, such as modification of the feel, and/or protection against external attacking factors such as light or heat. These properties may be readily eliminated, re-obtained, or even changed, via washing operations and simple reapplication of beneficial agents bearing anionic group(s).

Furthermore, said process improves the durability of colouring effects with respect to shampooing.

For the purposes of the present invention, the term "beneficial agent" means a cosmetic treatment agent that is capable of giving keratin fibres a cosmetic property, especially of protecting them, enhancing their beauty, conditioning them, treating them and/or holding them in shape.

For the purposes of the present invention, the term "anionic group" means a group bearing an acid function in neutralized or non-neutralized form. These anionic groups are preferably chosen from the following groups: $-CO_2H$, $-CO_2^-$, $-SO_3H$, $-SO_3^-$, $-OSO_3H$, $-OSO_3^-$, $-H_2PO_3$, $-HPO_3^-$, $-PO_3^{2-}$, $-H_2PO_2$, $-HPO_2^-$, $-PO_2^{2-}$, $-POH$ and $-PO^-$.

The beneficial agent(s) that may be used in the invention are especially chosen from:
(i) anionic surfactants and amphoteric or zwitterionic surfactants,
(ii) anionic sunscreens,
(iii) anionic polymers and amphoteric polymers; and
(iv) mixtures thereof.

As beneficial agent bearing anionic group(s), use may be made of one or more anionic surfactants or one or more amphoteric or zwitterionic surfactants.

The term "anionic surfactant" means a surfactant comprising, as ionic or ionizable groups, only anionic groups. These anionic groups are preferably chosen from the following groups: $-CO_2H$, $-CO_2^-$, $-SO_3H$, $-SO_3^-$, $-OSO_3H$, $-OSO_3^-$, $-H_2PO_3$, $-HPO_3^-$, $-PO_3^{2-}$, $-H_2PO_2$, $-HPO_2^-$, $-PO_2^{2-}$, $-POH$ and $-PO^-$.

Mention may be made, as examples of anionic surfactants that may be used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyltaurates, salts of alkyl monoesters of polyglycoside-polycarboxylic acids, acyl lactylates, D-galactoside-uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 40 carbon atoms and preferably from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactants are in the form of salts, they may be chosen from alkali metal salts such as the sodium or potassium salt and preferably the sodium salt, the ammonium salts, the amine salts and in particular the amino alcohol salts or the alkaline-earth metal salts such as the magnesium salt.

Examples of amino alcohol salts that may in particular be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxy-methyl)-aminomethane salts.

Alkali metal or alkaline-earth metal salts and in particular the sodium or magnesium salts are preferably used.

In one particular case, the anionic surfactants may be contained in crystals or emulsions of fatty substances. These crystals or emulsions especially comprise mixtures of fatty substances in an amount of from 1% to 15% by weight and of long-chain surfactants containing more than 14 carbon atoms in an amount of from 1% to 10%.

In a first variant, the anionic surfactants may be chosen from $(C_6$-$C_{24})$alkyl sulfates, $(C_6$-$C_{24})$alkyl ether sulfates comprising from 2 to 50 ethylene oxide units, especially in the form of alkali metal, ammonium, amino alcohol and alkaline-earth metal salts, or a mixture of these compounds.

Even better still, $(C_{12}$-$C_{20})$alkyl sulfates, $(C_{12}$-$C_{20})$alkyl ether sulfates comprising from 2 to 20 ethylene oxide units, in particular in the form of alkali metal, ammonium, amino alcohol and alkaline-earth metal salts, or a mixture of these compounds, are preferred in this variant. Better still, $(C_{12}$-$C_{20})$alkyl sulfates in the form of alkali metal, ammonium, amino alcohol and alkaline-earth metal salts are preferred, in particular sodium stearyl sulfate.

In a second variant, the anionic surfactants may be chosen from surfactants comprising anionic groups chosen from —C(O)OH, —C(O)O⁻, —SO₃H and —S(O)₂O⁻, such as alkylsulfonates, alkylamide sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates, N-acyltaurates, acyl lactylates, N-acylglycinates or alkyl ether carboxylates, the alkyl and acyl groups of all these compounds comprising from 6 to 40 carbon atoms and preferably from 6 to 24 carbon atoms.

Most particularly, use may be made of $(C_{6-40}$ acyl)glutamates, better still $(C_{6-24}$ acyl)glutamates, for instance the disodium cocoyl glutamate provided under the trade name Plantapon ACG LC by BASF, or $(C_{6-40}$ acyl)isethionates and better still $(C_{6-24}$ acyl)isethionates, for instance the sodium lauroyl methyl isethionate sold by Innospec under the trade name Iselux LQ-CLR-SB.

The amphoteric or zwitterionic surfactants that can be used in the present invention may especially be derivatives of optionally quaternized secondary or tertiary aliphatic amines containing at least one anionic group, for instance a carboxylate, sulfonate, sulfate, phosphate or phosphonate group, and in which the aliphatic group or at least one of the aliphatic groups is a linear or branched chain comprising from 8 to 22 carbon atoms.

Mention may be made in particular of $(C_8$-$C_{20})$alkylbetaines, sulfobetaines, $(C_8$-$C_{20})$alkylamido$(C_1$-$C_6)$alkylbetaines such as cocamidopropylbetaine, and $(C_8$-$C_{20})$alkylamido$(C_1$-$C_6)$alkylsulfobetaines.

Among the derivatives of optionally quaternized secondary or tertiary aliphatic amines that may be used, mention may also be made of the products having respective structures (V) and (VI) below:

$$R_a\text{—CONHCH}_2\text{CH}_2\text{—N}^+(R_b)(R_c)(\text{CH}_2\text{COO}^-) \qquad (V)$$

in which:
$R_a$ represents a $C_{10}$-$C_{30}$ alkyl or alkenyl group derived from an acid $R_a$—COOH preferably present in hydrolyzed coconut oil, or a heptyl, nonyl or undecyl group,
$R_b$ represents a β-hydroxyethyl group, and
$R_c$ represents a carboxymethyl group;

$$R_{a'}\text{—CONHCH}_2\text{CH}_2\text{—N(B)(B')} \qquad (VI)$$

in which:
B represents —CH₂CH₂OX',
X' represents the —CH₂—COOH, —CH₂—COOZ', —CH₂CH₂—COOH or —CH₂CH₂—COOZ' group or a hydrogen atom,
B' represents —(CH₂)$_z$—Y', with z=1 or 2,
Y' represents —COOH, —COOZ', or the group —CH₂—CHOH—SO₃H or —CH₂—CHOH—SO₃Z',
Z' represents an ion resulting from an alkali metal or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane,
$R_{a'}$ represents a $C_{10}$-$C_{30}$ alkyl or alkenyl group of an acid $R_{a'}$—COOH preferably present in coconut oil or in hydrolyzed linseed oil, an alkyl group, in particular of $C_{17}$ and its iso form, or an unsaturated $C_{17}$ group.

These compounds are also classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid and cocoamphodipropionic acid.

By way of example, mention may be made of the cocoamphodiacetate sold by Rhodia under the trade name Miranol® C2M Concentrate.

Use may also be made of compounds of formula (VIbis):

$$\begin{array}{l} R_{a''}\text{—NH—CH(Y'')—(CH}_2)_n\text{—C(O)—NH—(CH}_2) \\ \quad_{n'}\text{—N(R}_d)(R_e) \end{array} \qquad (VIbis)$$

in which formula:
Y" represents the group —C(O)OH, —C(O)OZ", —CH₂—CH(OH)—SO₃H or the group —CH₂—CH(OH)—SO₃—Z";
$R_d$ and $R_e$ represent, independently of each other, a $C_1$-$C_4$ alkyl or hydroxyalkyl group;
Z" represents a cationic counterion derived from an alkali metal or alkaline-earth metal, such as sodium, an ammonium ion or an ion derived from an organic amine;

R$_{a'''}$ represents a C$_{10}$-C$_{30}$ alkyl or alkenyl group of an acid R$_{a'''}$—C(O)OH preferably present in coconut oil or in hydrolyzed linseed oil;

n and n' denote, independently of each other, an integer ranging from 1 to 3;

Among the compounds of formula (VIbis), mention may be made of the compound classified in the CTFA dictionary under the name sodium diethylaminopropyl cocoaspartamide and sold by Chimex under the name Chimexane HB.

Preferably, the amphoteric or zwitterionic surfactants are chosen from (C$_8$-C$_{20}$)alkylbetaines, (C$_8$-C$_{20}$)alkylamido (C$_1$-C$_6$)alkylbetaines and (C$_8$-C$_{20}$)alkyl amphodiacetates, and mixtures thereof.

An anionic surfactant will preferably be used. Better still, use will be made of an anionic surfactant such as those comprising a sulfate or sulfonic group, and in particular sodium lauryl ether sulfate, sodium lauryl sulfate, ammonium lauryl sulfate and sodium stearyl sulfate.

The anionic sunscreen(s) that may be used as beneficial agent(s) bearing anionic group(s) are chosen especially from organic UVA- and/or UVB-screening agents as described below.

Organic UVA-screening Agents

A first example is benzene-1,4-bis(3-methylidene-10-camphorsulfonic acid) (INCI name: Terephthalylidene Dicamphor Sulfonic Acid) and the various salts thereof, described in particular in patent applications FR-A-2528420 and FR-A-2639347.

These screening agents correspond to general formula (XV) below:

(XV)

in which F denotes a hydrogen atom, an alkali metal or else a radical NH(R$_1$)$_3^+$ in which the radicals R1, which may be identical or different, denote a hydrogen atom, a C$_1$-C$_4$ alkyl or hydroxyalkyl radical or else a group Mn+/n, Mn+ denoting a polyvalent metal cation in which n is equal to 2 or 3 or 4, Mn+ preferably denoting a metal cation chosen from Ca$^{2+}$, Zn$^{2+}$, Mg$^{2+}$, Ba$^{2+}$, Al$^{3+}$ and Zr$^{4+}$. It is clearly understood that the compounds of formula (XV) above can give rise to the "cis-trans" isomer around one or more double bonds and that all the isomers fall within the context of the present invention.

Among the organic UVA-screening agents that can be used according to the present invention, mention may also be made of compounds comprising at least two benzazolyl groups bearing sulfonic groups, such as those described in patent application EP-A-0 669 323. They are described and prepared according to the syntheses indicated in patent U.S. Pat. No. 2,463,264 and also in patent application EP-A-0 669 323.

The compounds comprising at least two benzazolyl groups correspond to the general formula (XVI) below:

(XVI)

in which:
Z represents an organic residue of valency (1+n) comprising one or more double bonds placed such that it completes the system of double bonds of at least two benzazolyl groups as defined inside the square brackets so as to form a totally conjugated assembly;

X' denotes S, O or NR$^6$;

R$^1$ denotes hydrogen, C$_1$-C$_{18}$ alkyl, C$_1$-C$_4$ alkoxy, a C$_5$-C$_{15}$ aryl, a C$_2$-C$_{18}$ acyloxy, SO$_3$Y or COOY;

the radicals R$^2$, R$^3$, R$^4$ and R$^5$, which may be identical or different, denote a nitro group or a radical R$^1$;

R$^6$ denotes hydrogen, a C$_1$-C$_4$ alkyl or a C$_1$-C$_4$ hydroxyalkyl;

Y denotes hydrogen, Li, Na, K, NH$_4$, 1/2Ca, 1/2Mg, 1/3Al or a cation resulting from the neutralization of a free acid group with an organic nitrogenous base;

m is 0 or 1;

n is a number from 2 to 6;

l is a number from 1 to 4;

with the proviso that 1+n does not exceed the value 6.

Among these compounds, preference is given to those for which the group Z is chosen from the group made up of:

(a1) an olefin linear aliphatic C$_2$-C$_6$ hydrocarbon-based radical which may be interrupted with a C$_5$-C$_{12}$ aryl group or a C$_4$-C$_{10}$ heteroaryl group, in particular chosen from the following groups:

(b1) a C$_5$-C$_{15}$ aryl group which may be interrupted with an olefin linear aliphatic C$_2$-C$_6$ hydrocarbon-based radical, in particular chosen from the following groups:

(c1) a $C_3$-$C_{10}$ heteroaryl residue, in particular chosen from the following groups:

in which $R^6$ has the same meaning as that indicated above; said radicals Z as defined in paragraphs (a1), (b1) and (c1) possibly being substituted with $C_1$-$C_6$ alkyl, $C_1$-$C_6$ alkoxy, phenoxy, hydroxyl, methylenedioxy or amino radicals optionally substituted with one or two $C_1$-$C_5$ alkyl radicals.

Preferably, the compounds of formula (XVI) comprise, per molecule, 1, 3 or 4 groups $SO_3Y$.

As examples of compounds of formula (XVI) that may be used, mention may be made of the compounds of formulae (a') to (j') having the following structure, and also the salts thereof:

(a')

(b')

(c')

(d')

(e')

(f')

(g')

(h')

(i')

(j')

Among all these compounds, preference will most particularly be given to 1,4-bis-benzimidazolyl-phenylene-3,3', 5,5'-tetrasulfonic acid (INCI name: Disodium Phenyl Dibenzimidazole Tetrasulfonate) (compound (d')) or a salt thereof, having the following structure, sold under the name Neoheliopan AP® by Symrise:

Among the organic UVA-screening agents that may be used according to the present invention, mention may also be made of benzophenone compounds comprising at least one sulfonic acid function, for instance the following compounds:

Benzophenone-4, sold by BASF under the name Uvinul MS40®:

Benzophenone-5 having the structure

Benzophenone-9, sold by BASF under the name Uvinul DS49®:

Among the organic UVA-screening agents, use will more particularly be made of benzene-1,4-bis(3-methylidene-10-camphorsulfonic acid) and the various salts thereof (INCI name: Terephthalylidene Dicamphor Sulfonic Acid) produced by Chimex under the trade name Mexoryl SX®.

Organic UVB-Screening Agents

The organic UVB-screening agents are especially chosen from:
hydrophilic cinnamic derivatives such as ferulic acid or 3-methoxy-4-hydroxycinnamic acid,
hydrophilic benzylidenecamphor compounds,
hydrophilic phenylbenzimidazole compounds,
hydrophilic p-aminobenzoic (PABA) compounds,
hydrophilic salicylic compounds, and
mixtures thereof.

As examples of hydrophilic organic UVB-screening agents, mention may be made of those denoted hereinbelow under their INCI name:
para-aminobenzoic compounds:
  PABA,
  PEG-25 PABA, sold under the name Uvinul P 25® by BASF;
salicylic compounds:
  Dipropylene glycol salicylate sold under the name Dipsal® by Scher,
  TEA salicylate, sold under the name Neo Heliopan TS® by Symrise;
benzylidenecamphor compounds:
  Benzylidenecamphorsulfonic acid manufactured under the name Mexoryl SL® by Chimex,
  Camphor benzalkonium methosulfate manufactured under the name Mexoryl SO® by Chimex;
phenylbenzimidazole compounds:
  Phenylbenzimidazolesulfonic acid sold in particular under the trade name Eusolex 232® by Merck,

Use will more particularly be made of the screening agent phenylbenzimidazolesulfonic acid, sold especially under the trade name Eusolex 232® by Merck.

Preferably, the anionic sunscreens that may be used in the present invention are chosen from sulfonic screening agents, preferably from benzene-1,4-bis(3-methylidene-10-camphorsulfonic acid) and the various salts thereof; sulfonic benzophenone derivatives such as benzophenone-4; sulfonic benzylidenecamphor derivatives, such as benzylidenecamphorsulfonic acid; phenyl benzimidazole derivatives such as phenylbenzimidazolesulfonic acid and salts thereof, disodium phenyl dibenzimidazole tetrasulfonate; and mixtures thereof.

The composition according to the invention may comprise one or more polymers bearing anionic group(s) as beneficial agent(s) bearing anionic group(s). These polymers bearing anionic group(s) may be anionic or amphoteric polymers.

The anionic polymers generally used in the present invention are polymers comprising groups derived from carboxylic acids, sulfonic acids or phosphoric acids, and having a weight-average molecular mass of between 500 and 5 000 000.

The carboxylic groups may be provided by unsaturated mono- or dicarboxylic acid monomers, such as those corresponding to the formula:

(XVII)

in which n is an integer from 0 to 10, A denotes a methylene group, optionally linked to the carbon atom of the unsaturated group or to the neighbouring methylene group when n is greater than 1, via a heteroatom such as oxygen or sulfur, $R_1$ denotes a hydrogen atom, or a phenyl or benzyl group, $R_2$ denotes a hydrogen atom or a lower alkyl or carboxyl group, $R_3$ denotes a hydrogen atom, a lower alkyl group or a —$CH_2$—COOH, phenyl or benzyl group.

The term "lower alkyl" used in the invention means a $C_1$-$C_6$, preferably $C_1$-$C_4$ alkyl group.

In formula (XVII) above, an alkyl group preferably comprises from 1 to 4 carbon atoms and in particular denotes methyl and ethyl groups.

The anionic polymers containing carboxylic groups that are preferred according to the invention are:

A) acrylic or methacrylic acid homo- or copolymers, or salts thereof and in particular the products sold under the names Versicol® E or K by Allied Colloid and Ultrahold® by BASF, the copolymers of acrylic acid and of acrylamide sold in the form of their sodium salt under the names Reten® 421, 423 or 425 by Hercules, the sodium salts of polyhydroxycarboxylic acids.

B) copolymers of acrylic or methacrylic acids with a monoethylenic monomer such as ethylene, styrene, vinyl esters and acrylic or methacrylic acid esters, optionally grafted onto a polyalkylene glycol such as polyethylene glycol and optionally crosslinked. Such polymers are described in particular in French patent 1 222 944 and German patent application 2 330 956, the copolymers of this type comprising an optionally N-alkylated and/or hydroxyalkylated acrylamide unit in their chain, as described in particular in Luxembourgian patent applications 75370 and 75371 or provided under the name Quadramer by American Cyanamid. Mention may also be made of copolymers of acrylic acid and of $C_1$-$C_4$ alkyl methacrylate and the copolymer of methacrylic acid and of ethyl acrylate sold under the name Luvimer® MAEX by BASF.

C) copolymers derived from crotonic acid, such as those whose chain comprises vinyl acetate or propionate units and optionally other monomers such as allylic or methallylic esters, vinyl ether or vinyl ester of a saturated, linear or branched carboxylic acid containing a long hydrocarbon-based chain such as those comprising at least 5 carbon atoms, it being possible for these polymers to be grafted and crosslinked, or alternatively a vinyl, allylic or methallylic ester of an alpha- or beta-cyclic carboxylic acid. Such polymers are described, inter alia, in French patents Nos. 1 222 944, 1 580 545, 2 265 782, 2 265 781, 1 564 110 and 2 439 798. Commercial products that fall within this category are the resins 28-29-30, 26-13-14 and 28-13-10 sold by National Starch.

D) polymers derived from maleic, fumaric or itaconic acids or anhydrides with vinyl esters, vinyl ethers, vinyl halides, phenylvinyl derivatives or acrylic acid and esters thereof; these polymers may be esterified. Such polymers are described in particular in U.S. Pat. Nos. 2,047,398, 2,723,248 and 2,102,113 and GB patent 839 805, and especially those sold under the names Gantrez® AN or ES by ISP.

Polymers also falling within this category are the copolymers of maleic, citraconic or itaconic anhydrides and of an allylic or methallylic ester optionally comprising an acrylamide or methacrylamide group, an α-olefin, acrylic or methacrylic esters, acrylic or methacrylic acids or vinylpyrrolidone in their chain, the anhydride functions being monoesterified or monoamidated. These polymers are described, for example, in French patents 2 350 384 and 2 357 241 by the Applicant.

E) polyacrylamides comprising carboxylate groups.

F) The polymers comprising sulfonic groups are polymers comprising vinylsulfonic, styrenesulfonic, naphthalenesulfonic or acrylamidoalkylsulfonic units.

These polymers may be chosen especially from:
polyvinylsulfonic acid salts having a molecular mass of between approximately 1000 and 100 000, and also copolymers with an unsaturated comonomer, such as acrylic or methacrylic acids and esters thereof, and also acrylamide or derivatives thereof, vinyl ethers and vinylpyrrolidone;
polystyrenesulfonic acid salts and sodium salts having a molecular mass of about 500 000 and of about 100 000, sold, respectively, under the names Flexan® 500 and Flexan® 130 by National Starch. These compounds are described in patent FR 2198719;
polyacrylamidesulfonic acid salts, such as those mentioned in patent U.S. Pat. No. 4,128,631 and more particularly the polyacrylamidoethylpropanesulfonic acid sold under the name Cosmedia Polymer® HSP 1180 by Henkel.

G) anionic silicones.

Preferably, the anionic polymers are chosen from (meth) acrylic polymers and sulfonic polymers, such as those of families A), B) and F), better still from (meth)acrylic polymers.

According to the invention, the anionic polymers are even more particularly chosen from acrylic acid copolymers such as the acrylic acid/ethyl acrylate/N-tert-butylacrylamide terpolymer sold under the name Ultrahold Strong® by BASF, the copolymers of methacrylic acid and of methyl methacrylate sold under the name Eudragit® L by Röhm Pharma, the copolymer of methacrylic acid and of ethyl acrylate sold under the name Luvimer® MAEX by BASF, and from copolymers derived from crotonic acid, such as the vinyl acetate/vinyl tert-butylbenzoate/crotonic acid terpolymers and the crotonic acid/vinyl acetate/vinyl neododecanoate terpolymers sold especially under the name Resyn 28-2930 by AkzoNobel.

Better still, the anionic polymers are chosen from the copolymers of methacrylic acid and of methyl methacrylate sold under the name Eudragit® L by Röhm Pharma, and the copolymer of methacrylic acid and of ethyl acrylate sold under the name Luvimer® MAEX by BASF.

According to the invention, use may also be made of anionic latices or pseudolatices, i.e. aqueous dispersions of insoluble polymer particles.

It is also possible to use amphoteric polymers as beneficial agents bearing anionic group(s).

The amphoteric polymers may be chosen from polymers comprising units deriving:
a) from at least one monomer chosen from acrylamides and methacrylamides substituted on the nitrogen atom by an alkyl group,
b) from at least one acidic comonomer containing one or more reactive carboxylic groups, and
c) from at least one basic comonomer such as esters with primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides that are more particularly preferred according to the invention are compounds in which the alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are more particularly chosen from acrylic acid, methacrylic acid, crotonic acid, itaconic acid, maleic acid and fumaric acid and alkyl monoesters, containing 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers of which the INCI name is Octylacrylamide/acrylates/butylaminoethyl methacrylate copolymer, such as the products sold under the names Amphomer®, Amphomer® LV71 or Balance® 47 by Akzo Nobel, are particularly used.

The amphoteric polymers may also be chosen from amphoteric polymers comprising the repetition of:
(i) one or more units derived from a (meth)acrylamide-type monomer,
(ii) one or more units derived from a monomer of (meth) acrylamidoalkyltrialkylammonium type, and
(iii) one or more units derived from a (meth)acrylic acid-type acid monomer.

Preferably, the units derived from a monomer of (meth) acrylamide type are units of structure (XVIII) below:

(XVIII)

in which $R_1$ denotes H or $CH_3$ and $R_2$ is chosen from an amino, dimethylamino, tert-butylamino, dodecylamino and —NH—$CH_2$OH radical.

Preferably, said amphoteric polymer comprises the repetition of only one unit of formula (XVIII).

The unit derived from a monomer of (meth)acrylamide type of formula (XVIII) in which $R_1$ denotes H and $R_2$ is an amino radical ($NH_2$) is particularly preferred. It corresponds to the acrylamide monomer itself.

Preferably, the units derived from a monomer of (meth)acrylamidoalkyltrialkylammonium type are units of structure (XIX) below:

(XIX)

in which:
$R_3$ denotes H or $CH_3$,
$R_4$ denotes a group —$(CH_2)_k$— with k being an integer ranging from 1 to 6 and preferably from 2 to 4;
$R_5$, $R_6$ and $R_7$, which may be identical or different, denote a $C_1$-$C_4$ alkyl,
$Y^-$ is an anion such as bromide, chloride, acetate, borate, citrate, tartrate, bisulfate, bisulfite, sulfate or phosphate.

Preferably, said amphoteric polymer comprises the repetition of only one unit of formula (XIX).

Among these units derived from a monomer of (meth)acrylamidoalkyltrialkylammonium type of formula (XIX), the ones that are preferred are those derived from the methacrylamidopropyltrimethylammonium chloride monomer, for which $R_3$ denotes a methyl radical, k is equal to 3, $R_5$, $R_6$ and $R_7$ denote a methyl radical, and $Y^-$ denotes a chloride anion.

Preferably, the units derived from a monomer of (meth)acrylic acid type are units of formula (XX):

(XX)

in which $R_8$ denotes H or $CH_3$ and $R_9$ denotes a hydroxyl radical or an —NH—$C(CH_3)_2$—$CH_2$—$SO_3H$ radical.

The preferred units of formula (XX) correspond to the acrylic acid, methacrylic acid and 2-acrylamino-2-methylpropanesulfonic acid monomers.

Preferably, the unit derived from a monomer of (meth)acrylic acid type of formula (XX) is that derived from acrylic acid, for which $R_8$ denotes a hydrogen atom and $R_9$ denotes a hydroxyl radical.

The acidic monomer(s) of (meth)acrylic acid type may be non-neutralized or partially or totally neutralized with an organic or mineral base.

Preferably, said amphoteric polymer comprises the repetition of only one unit of formula (XX).

According to a preferred embodiment of the invention, the amphoteric polymer or polymers of this type comprise at least 30 mol % of units resulting from a monomer of (meth)acrylamide type (i). Preferably, they comprise from 30 mol % to 70 mol % and more preferably from 40 mol % to 60 mol % of units derived from a monomer of (meth)acrylamide type.

The content of units derived from a monomer of (meth)acrylamidoalkyltrialkylammonium type (ii) may advantageously be from 10 mol % to 60 mol % and preferentially from 20 mol % to 55 mol %.

The content of units derived from an acidic monomer of (meth)acrylic acid type (iii) may advantageously be from 1 mol % to 20 mol % and preferentially from 5 mol % to 15 mol %.

According to a particularly preferred embodiment of the invention, the amphoteric polymer of this type comprises:
from 30 mol % to 70 mol % and more preferably from 40 mol % to 60 mol % of units resulting from a monomer of (meth)acrylamide type (i),
from 10 mol % to 60 mol % and preferably from 20 mol % to 55 mol % of units resulting from a monomer of (meth)acrylamidoalkyltrialkylammonium type (ii), and
from 1 mol % to 20 mol % and preferentially from 5 mol % to 15 mol % of units derived from a monomer of (meth)acrylic acid type (iii).

Amphoteric polymers of this type may also comprise additional units, other than the units derived from a monomer of (meth)acrylamide type, of (meth)acrylamidoalkyltrialkylammonium type and of (meth)acrylic acid type as described above.

However, according to a preferred embodiment of the invention, said amphoteric polymers are constituted solely of units derived from monomers of (meth)acrylamide type (i), of (meth)acrylamidoalkyltrialkylammonium type (ii) and of (meth)acrylic acid type (iii).

Mention may be made, as an example of particularly preferred amphoteric polymers, of acrylamide/methacrylamidopropyltrimethylammonium chloride/acrylic acid terpolymers. Such polymers are listed in the CTFA dictionary (INCI) under the name "Polyquatemium 53". Corresponding products are in particular sold under the names Merquat 2003 and Merquat 2003 PR by Nalco.

As another type of amphoteric polymer that may be used, mention may also be made of copolymers based on (meth)acrylic acid and on a dialkyldiallylammonium salt, such as copolymers of (meth)acrylic acid and of dimethyldiallylammonium chloride. An example that may be mentioned is Merquat 280 sold by Nalco.

Preferably, use is made of the copolymers whose INCI name is Octylacrylamide/acrylates/butylaminoethyl methacrylate copolymer, such as the products sold under the names Amphomer®, Amphomer® LV71 or Balance® 47 by AkzoNobel.

Preferably, the polymer(s) bearing anionic group(s) that may be used as beneficial agent(s) bearing anionic group(s) are one or more anionic polymers such as those described above, such as (meth)acrylic polymer(s), and mixtures thereof.

Preferably, the beneficial agent(s) bearing anionic group(s) are chosen from anionic surfactants such as those comprising a sulfate or sulfonic group, sulfonic sunscreens, and anionic polymers such as (meth)acrylic polymer(s), and mixtures thereof.

Better still, the beneficial agent(s) bearing anionic group(s) are chosen from sodium stearyl sulfate, sodium lauryl ether sulfate, sodium lauryl sulfate, ammonium lauryl sulfate, terephthalylidenedicamphorsulfonic acid, acrylic acid/ethyl acrylate/N-tert-butylacrylamide terpolymers and vinyl acetate/vinyl tert-butylbenzoate/crotonic acid terpolymers and crotonic acid/vinyl acetate/vinyl neododecanoate terpolymers, and the octylacrylamide/acrylates/butylaminoethyl methacrylate copolymer, and mixtures thereof.

Said anionic beneficial agent(s) used in composition (B) according to the invention may represent from 0.001% to 20% by weight, preferably from 0.01% to 15% by weight and in particular from 0.05% to 10% by weight, relative to the total weight of composition (B).

Composition (B) preferably comprises a cosmetically acceptable medium which preferably comprises water, one or more organic solvents such as those described above for composition (A), or a mixture thereof.

Preferably, the amount of water ranges from 30% to 99.95% by weight, better still from 50% by weight to 99.92% by weight, even better still from 60% to 99.92% by weight and even more preferentially from 80% to 99% by weight, relative to the total weight of composition (B).

The pH of composition (B) is preferably between 3 and 11 and especially between 4 and 10.

Composition (B) according to the invention may also contain additives usually used in cosmetics, such as thickeners, preserving agents, fragrances and dyes, and also most of the usual cosmetic agents for hair treatments.

These additives may be present in composition (B) according to the invention in an amount ranging from 0 to 20% by weight, relative to the total weight of the composition.

In one particular embodiment, composition (A) is applied either before or after composition (B). An intermediate rinsing step may optionally take place between the application of compositions (A) and (B).

In a preferred variant of the invention, composition (A) is applied before composition (B). In another variant of the invention, composition (B) is applied before composition (A).

Composition (B) may be used on wet or dry hair, in rinse-off or leave-on mode.

Composition (B) is in the form of a lotion, a gel, an emulsion, a cream or a paste.

A heating step may be envisaged after the two compositions (A) and (B) have been applied, for example using a straightening iron regulated at a temperature preferably ranging from 150° C. to 230° C., better still from 200° C. to 220° C.

According to a preferred embodiment of the invention, the process will be performed by applying composition (A), intermediate drying, applying composition (B) and then rinsing and drying the hair.

The present invention also relates to a multi-compartment device, or kit, for treating keratin fibres, comprising at least two compartments:
 a first compartment containing a composition (A) as described in the present application; and
 a second compartment containing a composition (B) comprising one or more anionic beneficial agents.

In one variant, the device according to the invention comprises at least three compartments:
 a first compartment containing a composition (A1) comprising one or more alkoxysilanes bearing solubilizing function(s) (a) as described above; and
 a second compartment containing a composition (A2) comprising one or more alkylalkoxysilanes (b) as described above; and
 a third compartment containing a composition (B) comprising one or more anionic beneficial agents.

Compositions (A1), (A2) and (B) may comprise a cosmetically acceptable medium as described above.

Compositions (A1), (A2) and (B) may also comprise additives that are usually used in cosmetics, as described above.

The invention is illustrated by the examples that follow.

EXAMPLES

Example 1

The compositions according to the invention were prepared from the ingredients indicated in the table below. All the percentages are by weight and the amounts indicated are expressed as % by weight of product in its existing form, relative to the total weight of each composition.

|  | Formulation | | | |
| --- | --- | --- | --- | --- |
|  | 1 | 2 | 3 | 4 |
| Aminopropyltriethoxysilane | 5 | 5 | 5 | 5 |
| Methyltriethoxysilane | 1.5 | 1.5 | 1.5 | 1.5 |
| Lactic acid (90% of AM) | 3 | 3 | 3 | 3 |
| Isododecane | 25 | — | 12.5 | — |
| Cyclopentasiloxane | — | 25 | 12.5 | — |
| Octamethyltrisiloxane | — | — | — | 25 |
| Water qs | 100 | 100 | 100 | 100 |

AM: active material

Formulations 1 to 4 were prepared in the following manner: the methyltriethoxysilane was mixed with seven times its equivalent by volume of water which had been brought beforehand to pH 3 by addition of lactic acid. The mixture was then stirred for 30 minutes at room temperature.

In parallel, the aminopropyltriethoxysilane was diluted in the remaining amount of water, and the remaining amount of lactic acid was added. The solution obtained was stirred for 30 minutes, and the first solution was then added thereto. The fatty substances were then added to the mixture.

The formulations were applied to locks of natural or sensitized wet or dry hair, in an amount of 150 mg per gram of hair, in leave-in mode. In rinse-out mode, 400 mg per gram of hair were applied.

After a leave-on time of 5 minutes, the hair was dried, or was rinsed with water and then dried. The drying is natural, or else is facilitated by applying the heat of a hairdryer, optionally of flat tongs.

Very manageable, soft-feeling treated locks were thus obtained. They show good resistance to ambient moisture without becoming frizzy.

A care effect is very clearly perceptible during shampoo washes performed subsequently: markedly easier disentangling is observed.

Example 2

The compositions according to the invention are prepared from the ingredients indicated in the table below. All the percentages are by weight and the amounts indicated are expressed as % by weight of product in its existing form, relative to the total weight of each composition.

|  | Formulation | | | |
| --- | --- | --- | --- | --- |
|  | 5 | 6 | 7 | 8 |
| Aminopropyltriethoxysilane | 10 | 10 | 10 | 10 |
| Methyltriethoxysilane | 1.5 | 1.5 | 1.5 | 3 |

-continued

| | Formulation | | | |
|---|---|---|---|---|
| | 5 | 6 | 7 | 8 |
| Lactic acid (90% of AM) | 2.5 | 2.5 | 3.75 | 4 |
| Isododecane | — | — | 40 | 20 |
| Cetiol UT | 50 | — | — | — |
| Mineral oil | — | 40 | — | — |
| Sodium lauryl ether sulfate | — | — | 8 | — |
| Water qs | 100 | 100 | 100 | 100 |

AM: active material

Example 3

Formulation A according to the invention and comparative formulation B were prepared from the ingredients indicated in the table below. All the percentages are by weight and the amounts indicated are expressed as % by weight of active material, relative to the total weight of the formulation.

| | A (Invention) | B (Comparative) |
|---|---|---|
| Octyltriethoxysilane (Dynasilan OCTEO-EVONIK) | — | 3 |
| Methyltriethoxy silane (MTES) | 3 | — |
| Aminopropyltriethoxysilane (XIAMETER OFS-6011 SILANE-DOW CORNING) | 10 | 10 |
| Cetylstearylic alcool (C16/C18 50/50) | 5 | 5 |
| Mixture of myristyl stearate and of myristyl palmitate (INCI name: CETYL ESTERS (and) CETYL ESTERS, sold under the commercial tradename MIRACETI by LASERSON) | 1 | 1 |
| 2-phenoxyethanol | 0.5 | 0.5 |
| Lactic acid | 4 | 4 |
| Behenyl trimethyl ammonium chloride | 0.79 | 0.79 |
| Polydimethylsiloxane with aminoethylaminopropyl groups, methoxy and/or hydroxy and alpha-omega silanols functions | 0.86 | 0.86 |
| Hydroxyethylcellulose | 1 | 1 |
| Eau | Qs 100 | Qs 100 |

Locks of curly natural hair of 2.7 g were washed with a standard shampoo such as DOP Camomille, rinsed and wrung out.

0.4 g. of composition A or B was applied. The locks are then dried naturally.

An evaluation of the locks was carried out in term of humidity resistance.

Figure 1A:
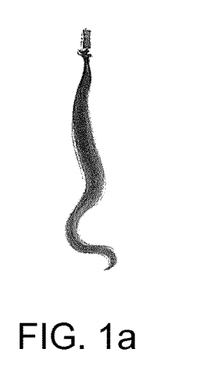
FIG. 1a is a photo of a lock treated with a composition according to the invention, before being placed under a humid atmosphere.
Figure 1B:
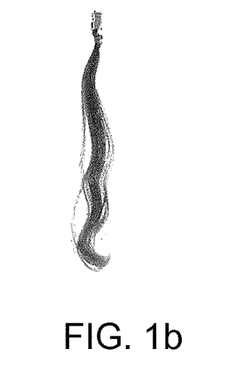
FIG. 1b is a photo of a lock treated with a comparative composition, before being placed under a humid atmosphere.

The locks were first disentangled and photos of them were taken. FIG. 1a shows a lock treated with composition A according to the invention while FIG. 1b shows a lock treated with comparative composition B.

Then, the locks were put under a humid atmosphere, 80% relative humidity at 25° C. for 24 hours. They were disentangled once again and photographed as seen in FIGS. 2a and 2b.

Figure 2A:
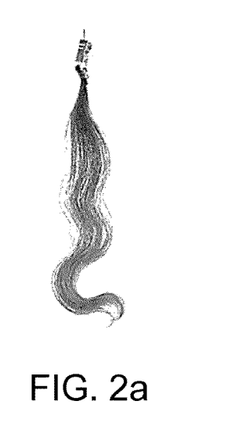
FIG. 2a is a photo of a lock treated with a composition according to the invention, and having undergone a humid atmosphere.
Figure 2B:
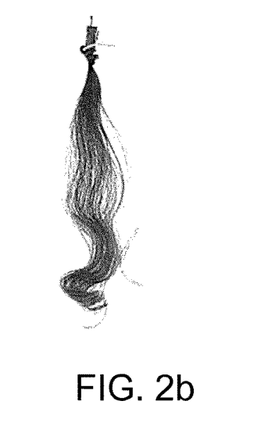
FIG. 2b is a photo of a lock treated with a similar process using a comparative composition, and having undergone a humid atmosphere.

FIG. 2a shows that the lock treated with composition A according to the invention has a better volume control and manageability than that of FIG. 2b which was treated with comparative composition B. The loss of the shape and formation of frizz were decreased with composition A according to the invention.

Consequently, the lock treated with composition A resists humidity better than the lock treated with comparative composition B.

The invention claimed is:

1. A composition comprising:
(a) at least one alkoxysilane bearing at least one solubilizing function of formula (I) below, and/or oligomers thereof, said oligomers comprising from 2 to 10 silicon atoms:

$$R_1Si(OR_2)_z(R_3)_x(OH)_y \quad (I)$$

wherein:
$R_1$ is a linear or branched, saturated or unsaturated, cyclic or acyclic $C_1$-$C_6$ hydrocarbon-based chain substituted with one or more groups chosen from the following groups:
amine $NH_2$ or NHR, R being:
a $C_1$-$C_{20}$ alkyl group optionally substituted with a group comprising a silicon atom,
a $C_3$-$C_{40}$ cycloalkyl group, or
a $C_6$-$C_{30}$ aromatic group,
hydroxyl,
thiol,
aryl or aryloxy substituted with an amino group or with a $C_1$-$C_4$ aminoalkyl group,
$R_1$ optionally being interrupted with a heteroatom chosen from O, S or NH, or a carbonyl group (CO),
$R_2$ and $R_3$, which may be identical or different, each represent a linear or branched alkyl group comprising from 1 to 6 carbon atoms,
y denotes an integer ranging from 0 to 3,
z denotes an integer ranging from 0 to 3, and
x denotes an integer ranging from 0 to 2,
with the proviso that z+x+y=3,
(b) at least one alkylalkoxysilane of formula (III) below, and/or oligomers thereof, said oligomers comprising from 2 to 10 silicon atoms:

$$(R_4)_mSi(OR_5)_n \quad (III)$$

wherein:
$R_4$ and $R_5$ each represent, independently of each other, a $C_{1-6}$ alkyl group,
n ranges from 1 to 3,
m ranges from 1 to 3,
with the proviso that m+n=4, and
(c) at least one fatty substance.

2. The composition according to claim 1, wherein $R_1$ is a linear or branched, saturated or unsaturated $C_1$-$C_6$ hydrocarbon-based chain, substituted with an amine group $NH_2$ or NHR, R being:
a $C_1$-$C_{20}$ alkyl group optionally substituted with a group comprising a silicon atom,
a $C_3$-$C_{40}$ cycloalkyl group, or
a $C_6$-$C_{30}$ aromatic group.

3. The composition according to claim 1, wherein $R_2$ represents an alkyl group comprising from 1 to 4 carbon atoms.

4. The composition according to claim 1, wherein the alkoxysilane bearing at least one solubilizing function (a) is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane and bis[3-(triethoxysilyl)propyl]amine, oligomers thereof or mixtures thereof.

5. The composition according to claim 1, wherein the alkoxysilane bearing at least one solubilizing function (a) is chosen from those of formula (II) and/or oligomers thereof:

$$H_2N(CH_2)_{n''}\text{—}Si(OR')_3 \quad (II)$$

wherein the groups R', which may be identical or different, are each chosen from linear or branched $C_1$-$C_6$ alkyl groups and n'' is an integer ranging from 1 to 6.

6. The composition according to claim 1, wherein the alkoxysilane bearing at least one solubilizing function (a) is present in an amount ranging from 0.5% to 50% by weight, relative to the total weight of the composition.

7. The composition according to claim 1, wherein, in formula (III), $R_5$ represents a methyl, ethyl or n-propyl group; n=3; and m=1.

8. The composition according to claim 1, wherein the alkylalkoxysilane (b) is chosen from methyltriethoxysilane (MTES), methyltripropylsilane, oligomers thereof.

9. The composition according to claim 1, wherein the alkylalkoxysilane (b) is present in an amount ranging from 0.1% to 50% by weight, relative to the total weight of the composition.

10. The composition according to claim 1, wherein compounds (a) and (b) are present in an (a)/(b) weight ratio ranging from 0.5 to 10.

11. The composition according claim 1, wherein the fatty substance (c) is liquid.

12. The composition according to claim 11, wherein the liquid fatty substance is chosen from linear or branched $C_6$-$C_{16}$ alkanes, undecane, tridecane, isododecane, or mixtures thereof; triglyceride oils of plant origin, copra oil, or avocado oil; fatty esters or isopropyl myristate; branched fatty alcohols; linear or cyclic volatile silicones, comprising less than 7 silicon atoms; or mixtures thereof.

13. The composition according to claim 1, wherein the fatty substance (c) is present in an amount of greater than or equal to 3% by weight, relative to the total weight of the composition.

14. The composition according to claim 1, further comprising a cosmetically acceptable medium comprising water, at least one organic solvent, or a mixture thereof.

15. A process for shaping and/or conditioning the hair, the process comprising applying to the hair an effective amount of a composition (A) comprising:
(a) at least one alkoxysilane bearing at least one solubilizing function of formula (I) below, and/or oligomers thereof, said oligomers comprising from 2 to 10 silicon atoms:

$$R_1Si(OR_2)_z(R_3)_x(OH)_y \quad (I)$$

wherein:
$R_1$ is a linear or branched, saturated or unsaturated, cyclic or acyclic $C_1$-$C_6$ hydrocarbon-based chain substituted with one or more groups chosen from the following groups:
amine $NH_2$ or NHR, R being:
a $C_1$-$C_{20}$ alkyl group optionally substituted with a group comprising a silicon atom,
a $C_3$-$C_{40}$ cycloalkyl group, or
a $C_6$-$C_{30}$ aromatic group,
hydroxyl,
thiol,
aryl or aryloxy substituted with an amino group or with a $C_1$-$C_4$ aminoalkyl group,
$R_1$ optionally being interrupted with a heteroatom chosen from O, S or NH, or a carbonyl group (CO),
$R_2$ and $R_3$, which may be identical or different, each represent a linear or branched alkyl group comprising from 1 to 6 carbon atoms,
y denotes an integer ranging from 0 to 3,
z denotes an integer ranging from 0 to 3, and
x denotes an integer ranging from 0 to 2,
with the proviso that z+x+y=3,
(b) at least one alkylalkoxysilane of formula (III) below, and/or oligomers thereof, said oligomers comprising from 2 to 10 silicon atoms:

$$(R_4)_mSi(OR_5)_n \quad (III)$$

wherein:
$R_4$ and $R_5$ each represent, independently of each other, a $C_{1-6}$ alkyl group,
n ranges from 1 to 3,
m ranges from 1 to 3,
with the proviso that m+n=4, and
(c) at least one fatty substance.

16. A cosmetic treatment process, the process comprising: applying to the hair an effective amount of a composition (A) comprising:
(a) at least one alkoxysilane bearing at least one solubilizing function of formula (I) below, and/or oligomers thereof, said oligomers comprising from 2 to 10 silicon atoms:

$$R_1Si(OR_2)_z(R_3)_x(OH)_y \quad (I)$$

wherein:
$R_1$ is a linear or branched, saturated or unsaturated, cyclic or acyclic $C_1$-$C_6$ hydrocarbon-based chain substituted with one or more groups chosen from the following groups:
amine $NH_2$ or NHR, R being:
a $C_1$-$C_{20}$ alkyl group optionally substituted with a group comprising a silicon atom,
a $C_3$-$C_{40}$ cycloalkyl group, or
a $C_6$-$C_{30}$ aromatic group,
hydroxyl,
thiol,
aryl or aryloxy substituted with an amino group or with a $C_1$-$C_4$ aminoalkyl group,
$R_1$ optionally being interrupted with a heteroatom chosen from O, S or NH, or a carbonyl group (CO),
$R_2$ and $R_3$, which may be identical or different, each represent a linear or branched alkyl group comprising from 1 to 6 carbon atoms,
y denotes an integer ranging from 0 to 3,
z denotes an integer ranging from 0 to 3, and
x denotes an integer ranging from 0 to 2,
with the proviso that z+x+y=3,
(b) at least one alkylalkoxysilane of formula (III) below, and/or oligomers thereof, said oligomers comprising from 2 to 10 silicon atoms:

$$(R_4)_mSi(OR_5)_n \quad (III)$$

wherein:
$R_4$ and $R_5$ each represent, independently of each other, a $C_{1-6}$ alkyl group,
n ranges from 1 to 3,
m ranges from 1 to 3,
with the proviso that m+n=4, and
(c) at least one fatty substance, and optionally rinsing.

* * * * *